United States Patent
Smith et al.

(10) Patent No.: US 7,945,318 B2
(45) Date of Patent: May 17, 2011

(54) PERIPHERAL IMPEDANCE PLETHYSMOGRAPHY ELECTRODE AND SYSTEM WITH DETECTION OF ELECTRODE SPACING

(75) Inventors: Michael Smith, Oradell, NJ (US); Lloyd A. Marks, Westfield, NJ (US)

(73) Assignee: Smithmarks, Inc., Ridgefield, NJ (US)

( * ) Notice: Subject to any disclaimer, the term of this patent is extended or adjusted under 35 U.S.C. 154(b) by 0 days.

(21) Appl. No.: 12/404,933

(22) Filed: Mar. 16, 2009

(65) Prior Publication Data
US 2009/0177099 A1 Jul. 9, 2009

Related U.S. Application Data

(62) Division of application No. 10/392,308, filed on Mar. 20, 2003, now abandoned.

(51) Int. Cl.
*A61B 5/05* (2006.01)
*A61B 5/04* (2006.01)
(52) U.S. Cl. ............... 600/547; 600/382; 600/384
(58) Field of Classification Search ............ 600/300, 600/372, 382, 384, 481, 504, 505, 506, 507, 600/547; 340/540, 573.1; 73/1.01, 1.16
See application file for complete search history.

(56) References Cited

U.S. PATENT DOCUMENTS

| | | | |
|---|---|---|---|
| 3,957,037 A | 5/1976 | Fletcher |
| 3,994,284 A | 11/1976 | Voelker |
| 4,166,455 A | 9/1979 | Findl et al. |
| 4,674,518 A | 6/1987 | Salo |
| 4,848,351 A | 7/1989 | Finch |
| 5,353,793 A | 10/1994 | Bornn |
| 5,566,672 A | 10/1996 | Faasse, Jr. |
| 5,727,550 A | 3/1998 | Montecalvo |
| 6,015,389 A | 1/2000 | Brown |
| 6,066,139 A | 5/2000 | Ryan et al. |
| 6,128,518 A | 10/2000 | Billings et al. |

FOREIGN PATENT DOCUMENTS
EP 0 216 455 7/1986
WO WO 98/58681 6/1998

OTHER PUBLICATIONS

*Bioelectromagnetism, Principles and Applications of Bioelectric and Biomagnetic Fields*, Jaakko Malmivuo and Robert Plonsey, Oxford University Press, 1995, Chapter 25, "Impedance Plethysmography".

*Primary Examiner* — Jeffrey G Hoekstra
(74) *Attorney, Agent, or Firm* — Blank Rome LLP

(57) ABSTRACT

In a system and method for peripheral impedance plethysmography, an electrode for application to the patient's limb includes two outer current electrodes and two inner voltage electrodes. A distance between the two inner electrodes is automatically input into an analyzing device, either as a prestored value or as determined automatically from the electrode. Peripheral blood flow is calculated in accordance with that distance.

17 Claims, 5 Drawing Sheets

US 7,945,318 B2

PERIPHERAL IMPEDANCE PLETHYSMOGRAPHY ELECTRODE AND SYSTEM WITH DETECTION OF ELECTRODE SPACING

REFERENCE TO RELATED APPLICATION

The present application is a Divisional of U.S. patent application Ser. No. 10/392,308, filed Mar. 20, 2003, now abandoned, whose disclosure is hereby incorporated by reference in its entirety into the present disclosure.

FIELD OF THE INVENTION

The present invention is directed to an electrode, system and method for peripheral impedance plethysmography and more particularly to such an electrode, system and method in which the distance between the inner voltage electrodes is detected in one of several manners and need not be input manually.

DESCRIPTION OF RELATED ART

The measurement of peripheral blood flow is important in medicine, since there are many specific diseases in which peripheral blood flow is impaired, e.g., diabetes and atherosclerosis. Also, the peripheral blood flow is altered as the total cardiac output is increased or decreased. Cardiac output is particularly important in patients who are under anesthesia, are in the post-operative state, or are critically ill or unstable. As blood flow from the heart falls, the peripheral blood flow is dramatically reduced to preserve flow to the brain and vital organs.

Blood flow to an extremity can be measured painstakingly and invasively by dissecting out the main blood vessels to the limb (e.g., brachial artery in an arm) and encircling it with an electromagnetic flow probe. That is clearly not a technique suitable for clinical use. It is therefore desired to measure peripheral blood flow non-invasively.

Peripheral impedance (or conductance) plethysmography is a technique for non-invasively measuring peripheral blood flow by measuring peripheral pulse volume, which is the small change in the volume of a limb segment occurring within the cardiac cycle. The technique works by obtaining a raw pulse volume analog signal and applying a selective signal averaging algorithm to the raw pulse volume signal. The technique is described in U.S. Pat. No. 4,548,211 to Marks.

In the technique as currently practiced, the raw pulse volume analog signal is obtained by measuring the electrical impedance (or conductance) of a limb segment with an electrode such as that of FIG. 1. The electrode 102 is made of a flexible material 104, so that it can be wrapped around the limb. The flexible material is configured to define a connecting portion or vertical member 106, which is insulated from direct electrical contact with the patient, and two extending members 108 for being wrapped around or otherwise applied to the extremity. Each of the two extending members 108 contains an outer current electrode 110 paired with an inner voltage electrode 112. An electrical connector 114 allows the outer current electrodes 110 and the inner voltage electrodes 112 to be connected to a source of current and a voltage measuring device, respectively.

An alternating current on the order of 1 ma amplitude and 40 kHz frequency is applied to the two outer current electrodes, while the inner voltage electrodes are used to measure the voltage resulting from the applied current. The ratio of the amplitude of the voltage waveform to the amplitude of the current waveform is the limb impedance, Z. Measurements of Z over time provide the baseline impedance $Z_0$ of the limb segment and the pulsatile change $\Delta Z$ of the impedance. Once the resistivity $\rho$ of the blood and the distance L between the two inner voltage electrodes are known, the change in volume $\Delta V$ can be calculated as:

$$\Delta V = \rho L^2 \Delta Z / Z_0.$$

The resistivity $\rho$ is either calculated or approximated from the patient's hematocrit. The distance L must be measured with a measuring device, such as a ruler, and then the value of L must be manually input into the device which performs the calculations. That step is cumbersome and time-consuming. It is particularly a problem in one of the most important applications of peripheral impedance plethysmography, i.e., the management of trauma victims in whom hemorrhage has produced peripheral vasoconstriction. In that setting, it is desirable to apply the electrode to the patient and to obtain measurements in as few steps as possible.

The problem of measuring the spacing between electrodes in peripheral impedance plethysmography has been considered in U.S. Pat. No. 3,957,037 to Fletcher et al. That patent teaches a pair of readout ring electrodes for impedance plethysmography. The ring electrodes are held at a fixed distance from each other by a pair of rods. The rods have measurement indicia on them to permit visual inspection of the axial distance between them. However, Fletcher et al. do not teach or suggest automatic determination and input of that axial distance and thus do not offer a complete solution. Other previous patents, such as U.S. Pat. No. 4,166,455 to Findl et al, teach devices in which the electrodes are relatively movable; however, those previous devices suffer from the same deficiency previously noted for the Fletcher et al. device.

SUMMARY OF THE INVENTION

It will be readily apparent from the above that a need exists in the art to obtain the measurements automatically and in as few steps as possible. It is therefore an object of the invention to eliminate the need to measure L and to input the value manually.

It is another object of the invention to input L automatically, either by measuring it automatically or by using a pre-stored value.

To achieve the foregoing and other objects, the present invention is directed to an electrode, system and method for peripheral impedance plethysmography in which L is automatically determined, so that it is available for calculations without having to be input manually into the device. In various embodiments, L can have a single predetermined value, be determined from the electrode, or be calculated directly from the signals received from the electrode.

For limb impedance measurements, circumferential electrodes are preferable. Spot electrodes can be used to make impedance measurements, albeit less accurately. Of course, the shape of the electrode can be varied for any contemplated use.

Perhaps the simplest embodiment is a quadripolar, circumferential, electrode system, in which the electrodes are positioned at a known, fixed distance from one another. In this electrode configuration, the inner and outer electrodes are paired by attaching them to a common insulating base. The distance between the circumferential pairs is fixed. Such an electrode can be applied to a limb by attaching the vertical component to the limb, preferably the anterior aspect of the calf (or shin) with an adhesive exposed by a peel-off strip and then sequentially applying the proximal and distal circumferential electrodes around the limb, also with adhesive exposed by a peel-off strip. The distance between the inner electrodes is known and can therefore be preprogrammed as a default value into the device.

A modification of the first embodiment is to provide a number of different sizes of electrodes in which L varies, thus providing sizes for individuals with different sized limbs and, in addition, to provide a means to communicate the size of the electrode back to the device. This can be done, for example, by having the length L coded into the electrical connector that connects the electrode to the plethysmograph. Alternatively, this can be accomplished by having an additional pair of wires connecting the device and the electrode. A resistor of a particular value is incorporated into the electrode and attached to the additional leads. The device then reads the value of the resistor and uses a look-up table to determine which size electrode is being used.

A second, more complex, but more versatile embodiment allows the distal and proximal pairs of electrodes to be spaced at varying distances from one another, but with a means built into the electrode to measure L and to convey the measured value of L back to the device. The electrodes can, for example, be mounted on a rod and slidably positioned closer or farther from one another. A distance transducer, mechanically coupled to the electrodes, such as a rheostat, conveys the value of L back to the device so that it may be appropriately included in the calculations.

A third embodiment incorporates features from both the first and second embodiments. The vertical member is folded to reduce the distance between the inner electrodes to a minimum value. By unfolding the vertical member, the distance between the inner electrodes is increased to a greater value, thus providing more than one electrode spacing to accommodate different size limbs. A means is provided to indicate to the device, which of the lengths is active. One means to accomplish this is to provide an electrical connection that has continuity only when the vertical member is folded and is broken when the vertical member is unfolded and expanded to increase L. It is a straightforward technique to communicate this information to the device with an additional connection indicating the electrical continuity across the vertical member. Many other means can be employed to accomplish this task (e.g., capacitive coupling present only in the folded state).

A fourth embodiment uses an electronic means to actually calculate L. This allows the paired connectors to be positioned at arbitrary, varying distances from one another. For example, assume that the distance between the outer and inner electrodes in a given pair is d and the distance between the inner electrodes is L. If a current with amplitude I is applied to the outer electrodes, there will be voltage with amplitude $V_i$ detected between the inner electrodes and a voltage with amplitude $V_o$ between the outer electrodes. The ratio $V_o/V_i$ will be proportional to the distance between the outer electrodes divided by the distance between the inner electrodes or (L+2d)/L. Therefore, L may be calculated as $L=2dV_i/(V_o-V_i)$.

If it is desired to avoid using the exciting, outer current electrodes also as voltage electrodes, a modification of the fourth embodiment may be used. In this modification, a third electrode is added to each pair so that there is an outer, exciting, current electrode, a middle, measuring, voltage electrode and an inner "reference" electrode comprising each of the two electrode sets (proximal and distal). As before, the distance between the middle, measuring electrodes, L, is arbitrary. For this explanation, assume that the distance between the middle, measuring voltage electrode and the inner, reference electrode is d. If a current with amplitude I is applied to the outer electrodes, there will be voltage with amplitude $V_m$ detected between the middle electrodes and a voltage with amplitude $V_r$ between the inner, reference electrodes. The ratio $V_m/V_r$ is proportional to the distance between the middle, measuring electrodes divided by the distance between the inner, reference electrodes or L/(L−2d). Therefore, L may be calculated as $L=2dV_m/(V_m-V_r)$.

Similarly, this method can be employed using a single middle electrode positioned between the paired electrodes. If the distance between this electrode and one of the inner voltage electrodes is d, the voltage between the middle electrode and this inner voltage electrodes is $V_1$ and the voltage between the middle electrode and the other inner voltage electrode is $V_2$, then $d/V_1$ equals $L/(V_1+V_2)$ or $L=d(V_1+V_2)/V_1$.

BRIEF DESCRIPTION OF THE DRAWINGS

Various preferred embodiments of the invention will be set forth in detail with reference to the drawings, in which.

DETAILED DESCRIPTION OF THE PREFERRED EMBODIMENTS

Figure 1:
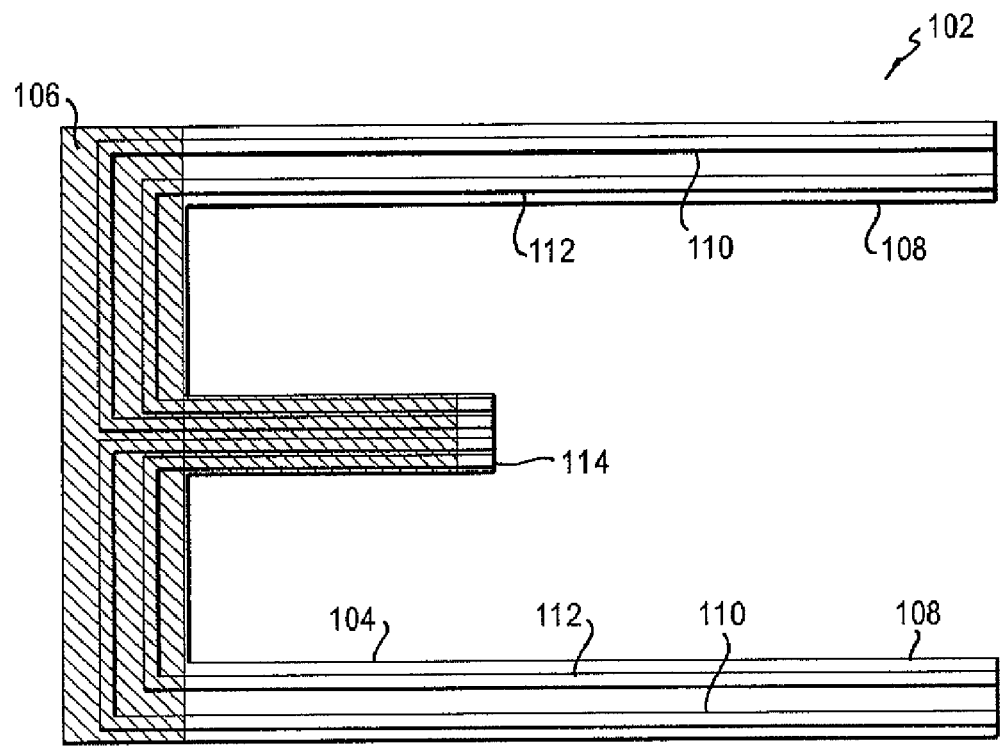
FIG. 1 shows an electrode for peripheral impedance plethysmography according to the prior art.

Various preferred embodiments of the invention will now be set forth in detail with reference to the drawings, in which like reference numerals refer to like elements throughout. In each of the preferred embodiments and the variations thereof, the electrode can be structured like the known electrode of FIG. 1, except for the modifications to be disclosed below.

Figure 2:
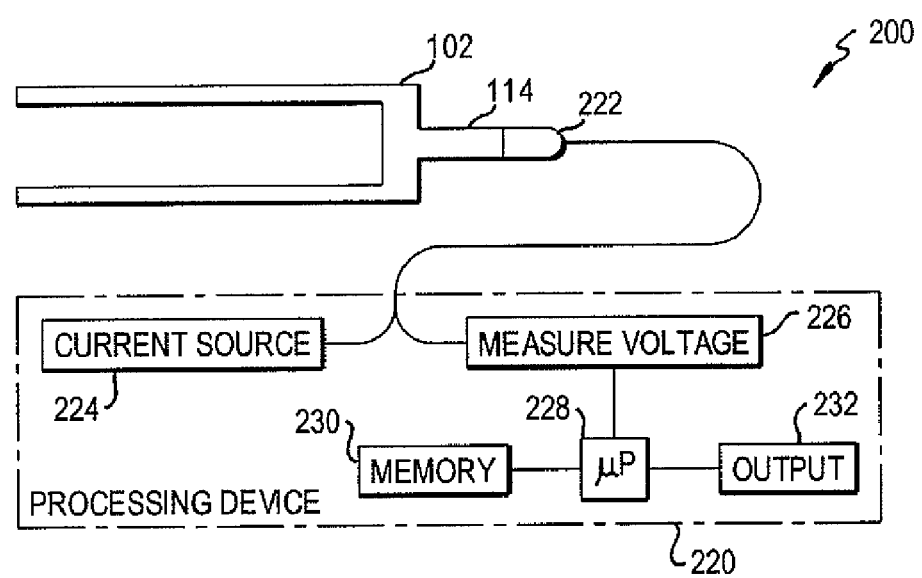
FIG. 2 shows a system for peripheral impedance plethysmography according to a first preferred embodiment of the present invention.

FIG. 2 shows a block diagram of a first preferred embodiment of the present invention. The system 200 uses an electrode 102 that is essentially similar to the electrode 102 of FIG. 1; in other words, the electrode of the prior art can be used without modification if desired. However, the processing device 220 is modified from those of the prior art in a manner to be explained below.

The electrode 102 and the processing device 220 are connected by way of electrical connectors 114, 222. In the processing device 220, a current source 224 applies alternating current to the two outer current electrodes to induce a voltage in the two inner voltage electrodes. In the processing device 220, a voltage measuring device 226 measures the induced voltage and supplies the measured value to a microprocessor 228 or other suitable processing element. The microprocessor 228 receives the value of L, the distance between the two inner voltage electrodes, from a memory 230, which can be a ROM, an EEPROM, or other suitable non-volatile memory. The microprocessor 228 uses that value of L to calculate ΔV and outputs the calculated value to any suitable output 232.

The first preferred embodiment, as described above, works with electrodes 102 having a single inter-electrode spacing. However, in practice, it is desirable to use electrodes of multiple inter-electrode spacings. Therefore, two variations of the first preferred embodiment having that capability will be described with reference to FIGS. 3-5.

Figure 3:
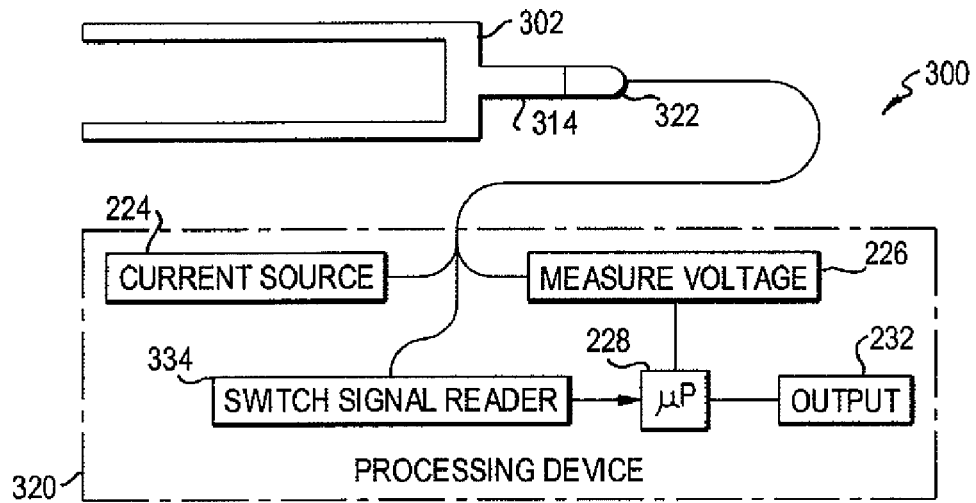
FIG. 3 shows a system for peripheral impedance plethysmography according to a first variation of the first preferred embodiment of the invention.
Figure 4:
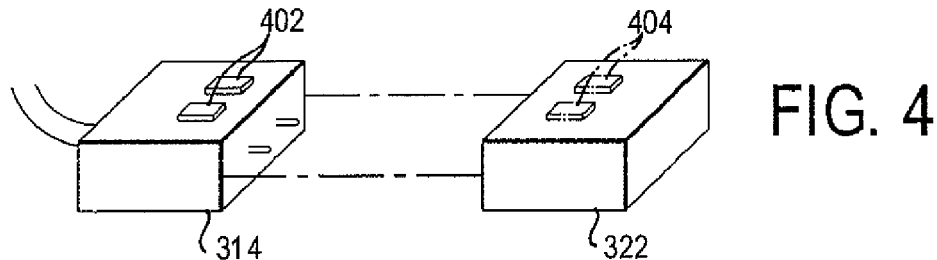
FIG. 4 shows electrical connectors used in the system of FIG. 3.

In the first variation of the first preferred embodiment, the system 300 of FIG. 3 does not use a memory such as that of the system 200 of FIG. 2. Instead, the electrode 302 can be any one of multiple electrodes having different values of L. Thus, the person using the system has flexibility in terms of choosing an electrode to accommodate the patient and the extremity in question. In the system 300, as shown in FIG. 4, the electrode 302 can be structured essentially like the electrode of the prior art, except that the electrical connector 314 of the electrode 302 has information on the distance L encoded into it. As one example, the encoding is mechanical, in the form of protrusions 402 which actuate mechanical switches 404 in the electrical connector 322 of the processing device 320, although any other suitable form of encoding can be used instead. The processing device 320 includes an element 334 that reads the encoding (e.g., by receiving signals from the mechanical switches) and outputs the reading of the encoding to the microprocessor 228, which thus knows L. The element 334 can include a look-up table or other suitable device for determining L from the switch signals.

Figure 5:
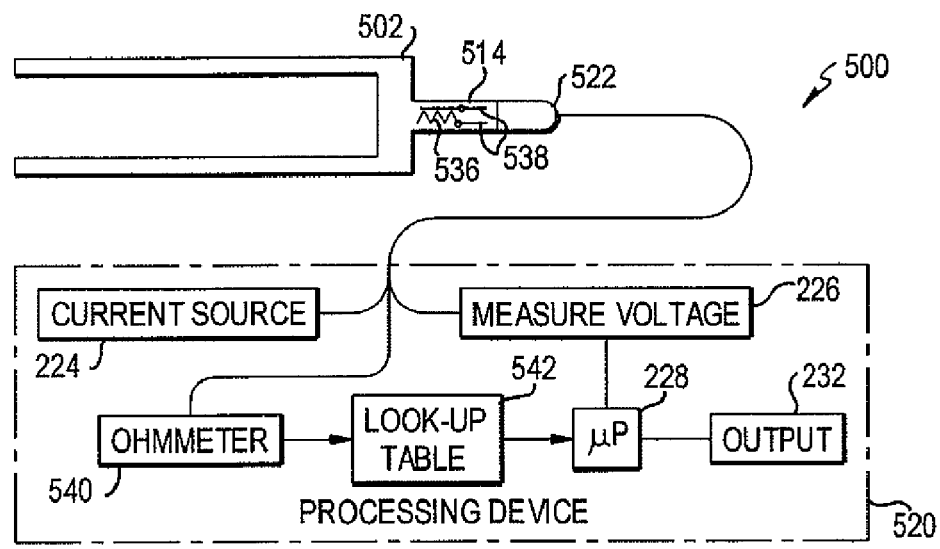
FIG. 5 shows a system for peripheral impedance plethysmography according to a second variation of the first preferred embodiment of the invention.

Similarly, in the second variation of the first preferred embodiment, in the system 500 of FIG. 5, the electrode 502 can be structured essentially like the electrode of the prior art except that the electrode 502 includes a resistor 536 whose resistance is chosen to represent L, as well as additional leads 538 for electrical connection of the resistor 536 through the electrical connectors 514, 522 to the processing device 520. In the processing device 520, an ohmmeter 540 determines the resistance and outputs the value to a look-up table 542 or other suitable device, which determines L and passes the value of L to the microprocessor 228.

The first preferred embodiment and its two variations presuppose that any given electrode has a single value of L. However, it is possible to construct electrodes with variable values of L and to construct processing devices that determine the variable value of L, thus providing greater flexibility of use. Preferred embodiments implementing such a feature will now be described.

Figure 6:
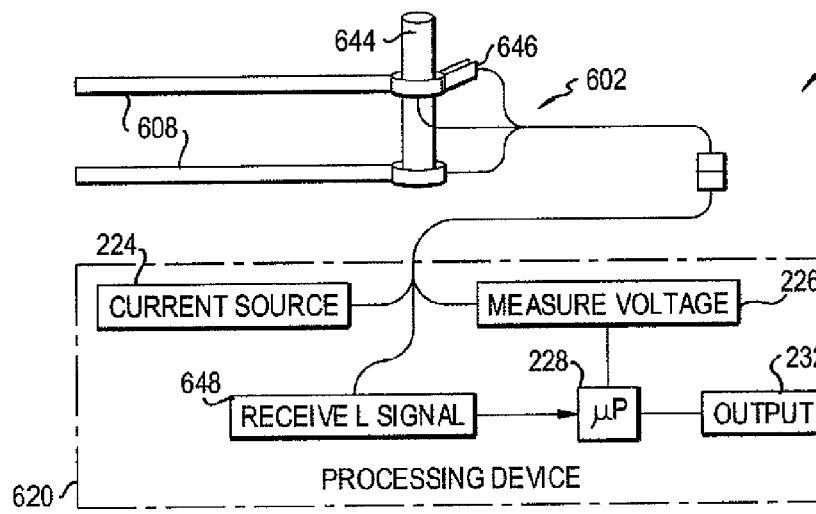
FIG. 6 shows a system for peripheral impedance plethysmography according to a second preferred embodiment of the invention.

In the second preferred embodiment, the electrode includes a component for determining L and outputting its value to the processing device. For example, as shown in FIG. 6, the system 600 includes an electrode 602 that is modified from the electrode of the prior art such that the two sets 608 of current and voltage electrodes are connected through a rod 644, somewhat similarly to what is disclosed in the aforesaid Fletcher et al patent. However, a distance transducer 646, such as a rheostat, is mechanically coupled to the two sets 608 of electrodes to measure L and to output that value to the processing device 620, which includes a component 648, such as an analog-to-digital converter, to receive that value and to transmit it to the microprocessor.

Figure 7:
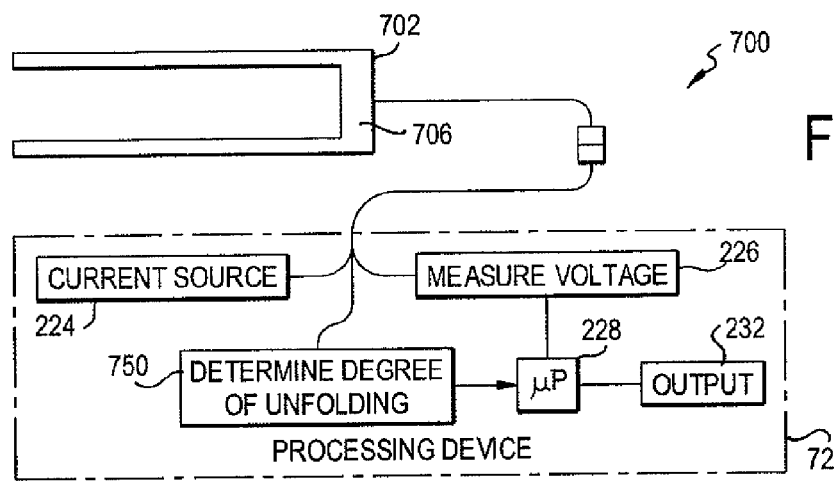
FIG. 7 shows a system for peripheral impedance plethysmography according to a third preferred embodiment of the invention.

The third preferred embodiment is similar, but does not require a rod or the complexities of a distance transducer. Instead, in the system 700 of FIG. 7, the electrode 702 is modified from the electrode of the prior art to have an electrical characteristic that changes as the connecting portion 706 is unfolded or unrolled. The processing device 720 includes a unit 750 for detecting the electrical characteristic to determine the extent to which the connecting portion 706 has been unfolded or unrolled and thus to determine L.

Various electrode designs which permit determination of the degree of unfolding or unrolling for use in the third preferred embodiment will now be described. The electrode designs can be based on the electrode of the prior art, except for the modifications to be set forth below.

Figure 8:
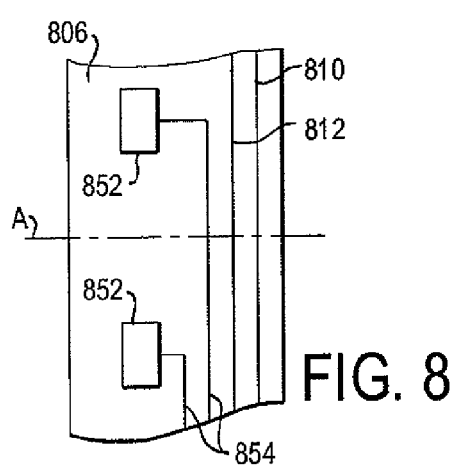
FIG. 8 shows a portion of an electrode usable with the system of FIG. 7.

FIG. 8 shows a portion of the connecting portion or vertical member 806 of one such electrode. In addition to the leads 810, 812 for the current and voltage electrodes, the vertical member 806 includes two exposed conductive pads 852, each with its own lead 854, one on either side of a folding line A. The exposed pads 852 are located on the opposite surface of the electrode from the surface that contacts the patient, so that the pads themselves do not contact the patient. When the vertical member 806 is folded along the fold line A, the pads are in direct electrical contact, whereas when the vertical member is unfolded, the contact is broken. Thus, the processing device can determine whether or not the vertical member has been unfolded by determining whether the direct electrical contact is intact or broken.

Figure 9:
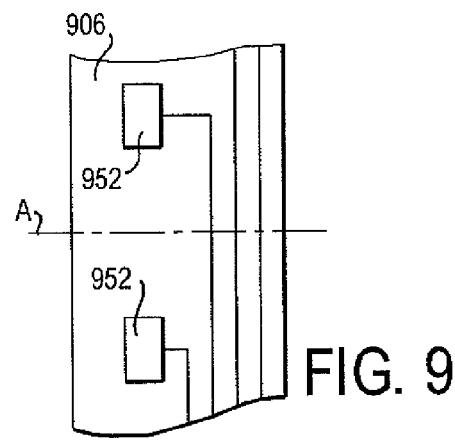
FIG. 9 shows a portion of another electrode usable with the system of FIG. 7.

FIG. 9 shows a portion of an essentially similar member 906, except that the pads 852 are not exposed at all. In that case, the contact to be detected is capacitive rather than direct. Of course, if the vertical member of FIG. 8 or FIG. 9 has multiple folding lines, multiple pairs of such pads can be provided.

Figure 10:
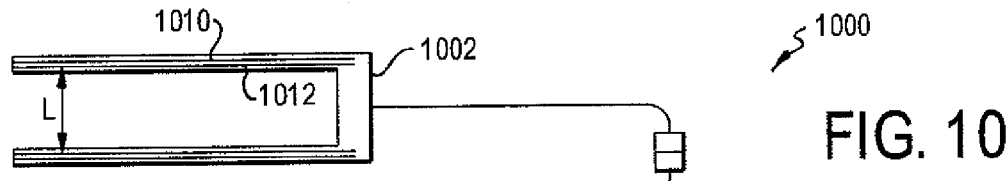
FIG. 10 shows a system for peripheral impedance plethysmography according to a fourth preferred embodiment of the invention.
Figure 10:
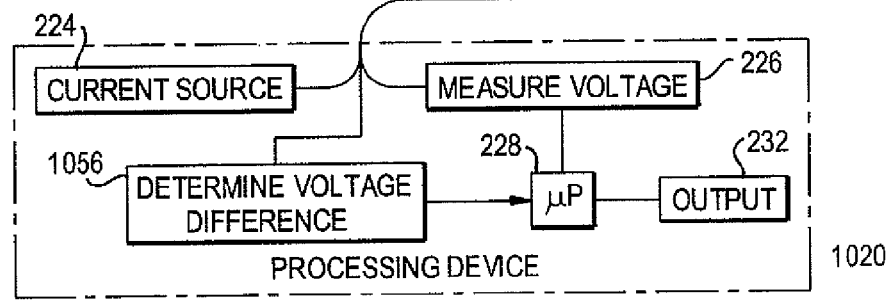

In a fourth preferred embodiment, L can be calculated directly. For example, as shown in the system 1000 of FIG. 10, assume that the distance between the outer and inner electrodes 1010, 1012 in a given pair in an electrode 1002 is d and the distance between the inner electrodes is L. If a current with amplitude I is applied to the outer electrodes, a voltage with amplitude $V_i$ will be detected between the inner electrodes and a voltage with amplitude $V_o$ will be detected between the outer electrodes. The ratio $V_o/V_i$ will be proportional to the distance between the outer electrodes divided by the distance between the inner electrodes or $(L+2d)/L$. Therefore, L may be calculated as $L=2dV_i/(V_o-V_i)$. In the system 1000, the processing device 1020 includes a component 1056 for determining $V_o$ and $V_i$ and supplying those values to the microprocessor. In the system of FIG. 10, the electrode of the prior art could be used without modification.

Figure 11:
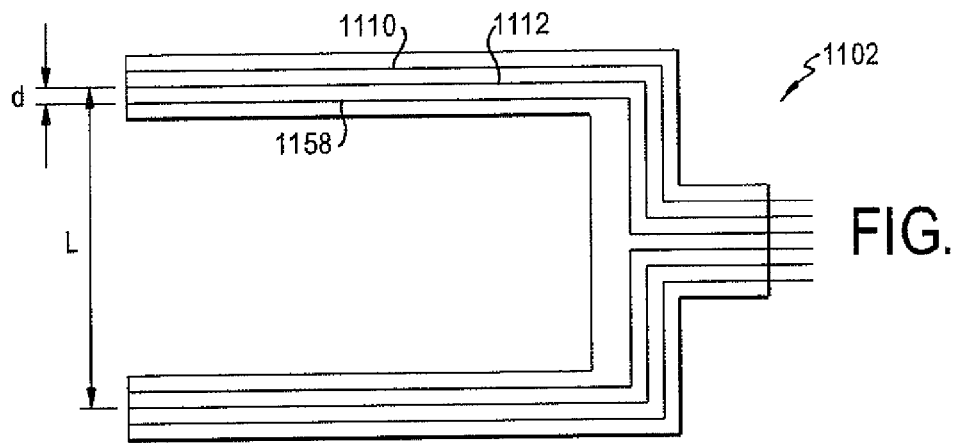
FIG. 11 shows an electrode for use with a first variation of the fourth preferred embodiment of the invention.

If it is desired to avoid using the exciting, outer, current electrodes also as voltage electrodes, a first variation of the fourth preferred embodiment may be used. In this modification, as shown in FIG. 11, the electrode 1102 is modified from the electrode of the prior art to add a third electrode 1158 to each pair so that there are an outer, exciting, current electrode 1110, a middle, measuring, voltage electrode 1112 and an inner reference electrode 1158. As before, the distance between the middle, measuring electrodes 1112, L is arbitrary. For this explanation, assume that the distance between the middle, measuring voltage electrode and the inner, reference electrode is d. If a current with amplitude I is applied to the outer electrodes, there will be voltage with amplitude $V_m$ detected between the middle electrodes and a voltage with amplitude $V_r$ between the inner, reference electrodes. The ratio $V_m/V_r$ is proportional to the distance between the middle, measuring electrodes divided by the distance between the inner, reference electrodes or $L/(L-2d)$. Therefore, L may be calculated as $L=2dV_m/(V_m-V_r)$.

Figure 12:
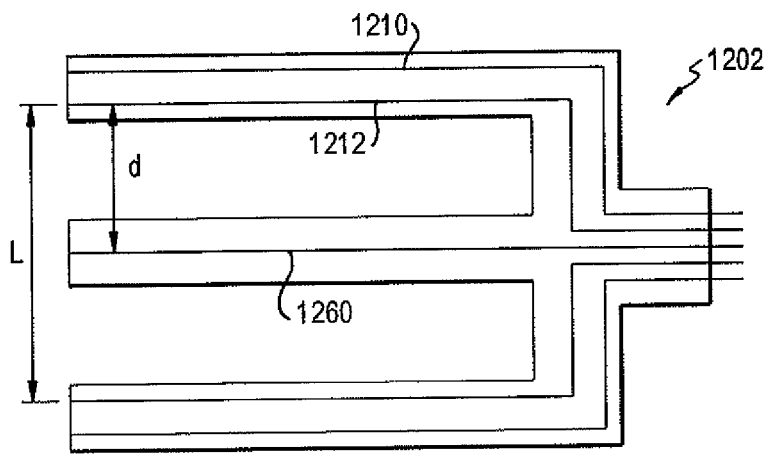
FIG. 12 shows an electrode for use with a second variation of the fourth preferred embodiment of the invention.

Similarly, as shown in FIG. 12, a second variation of the fourth preferred embodiment uses an electrode 1202 modified from the electrode of the prior art to have a single middle electrode 1260 positioned between the paired electrodes 1210, 1212. If the distance between this electrode 1260 and one of the inner voltage electrodes 1212 is d, the voltage between the middle electrode and one inner voltage electrode is $V_1$ and the voltage between the middle electrode and the other inner voltage electrode is $V_2$, then $d/V_1$ equals $L/(V_1+V_2)$ or $L=d(V_1+V_2)/V_1$.

Figure 13:
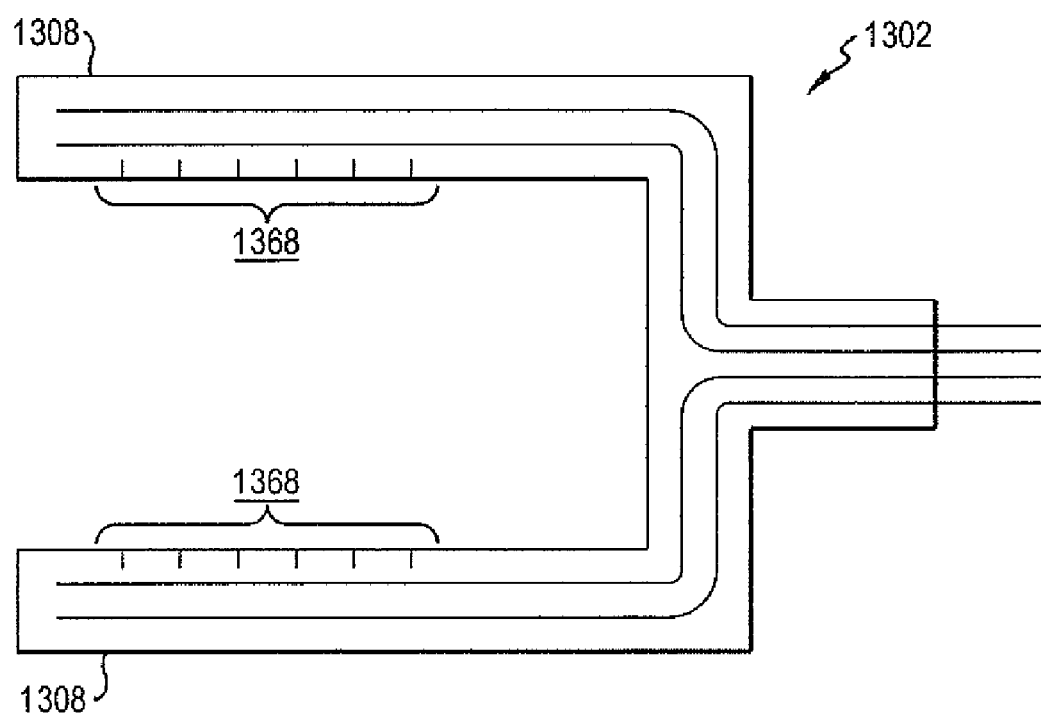
FIG. 13 shows an electrode for use with a modification of any of the preferred embodiments.

FIG. 13 shows a modification which can be used in the context of any of the preferred embodiments. In the modification of FIG. 13, not only is the distance L input, but also, a circumference of the extremity at a location to which one or both of the extending members are applied is determined and input. As shown in FIG. 13, one or both of the extending member 1308 include scales 1368 for measuring the circumference. The scales 1368 may be manually read, in which case the operator inputs the values into the processing device. Alternatively, they may be automatically read in a manner like that explained above with reference to FIGS. 8 and 9. Either way, the processing device performs the calculations in accordance with the measured circumference, e.g., by using the measured circumference and the distance L to calculate a cylindrical or frustro-conical volume.

While four preferred embodiments and variations thereon have been described above in detail, those skilled in the art who have reviewed the present disclosure will readily appreciate that other embodiments can be realized within the scope of the invention. Therefore, the invention should be construed as limited only by the appended claims.

We claim:

1. A method for peripheral impedance plethysmography, the method comprising:
   (a) attaching an electrode to an extremity of a patient, the electrode comprising two outer current electrodes and two inner voltage electrodes;
   (b) applying an alternating current to the two outer current electrodes;
   (c) measuring a voltage in each of the two inner voltage electrodes induced by the alternating current;
   (d) automatically receiving, in a processing device, the voltage measured in step (c) and a value of a distance between the two inner voltage electrodes, wherein the value of the distance is automatically received in the processing device by automatically generating a signal representing the value of the distance and automatically receiving the signal into the processing device; and
   (e) calculating, in the processing device, a volume change in the extremity in accordance with the voltage measured in step (c) and the value of the distance received in step (d) such that a result of said calculating depends on the value of the distance.

2. The method of claim 1, wherein the electrode is structured such that the distance between the inner voltage electrodes has a predetermined value, the predetermined value is previously stored in a medium accessible to the processing device, and step (d) comprises reading the predetermined value from the medium to produce said signal.

3. The method of claim 2, wherein the medium is part of the electrode, such that different electrodes having different values of the distance are usable with the processing device.

4. The method of claim 3, wherein the electrode comprises an electrical connector by which the electrode is connected to the processing device, and wherein the predetermined value is coded into the electrical connector such that the electrical connector constitutes the medium.

5. The method of claim 3, wherein the electrode comprises a resistor whose resistance corresponds to the predetermined value, and wherein step (d) comprises measuring the resistance and determining the predetermined value in accordance with the resistance.

6. The method of claim 5, wherein the predetermined value is determined in accordance with the resistance through a look-up table.

7. The method of claim 2, wherein the medium is part of the processing device.

8. The method of claim 1, wherein the electrode is structured such that the distance between the inner voltage electrodes has a variable value and step (d) comprises automatically determining the variable value.

9. The method of claim 8, wherein at least one of the electrode and the processing device comprises a distance measuring device for measuring the distance.

10. The method of claim 9, wherein the distance measuring device comprises a distance transducer in the electrode.

11. The method of claim 9, wherein the electrode further comprises a connecting portion connects the two inner voltage electrodes and which is structured to be unfolded to provide any of a plurality of values of the distance such that unfolding the connecting portion changes an electrical characteristic of the connecting portion, and the distance measuring device measures the distance by determining the electrical characteristic of the connecting portion.

12. The method of claim 11, wherein the electrical characteristic comprises a characteristic in which an electrical connection in the connecting portion is broken or not broken, and wherein the distance measuring device determines whether the electrical connection is broken or not broken.

13. The method of claim 12, wherein the electrical connection comprises a direct connection.

14. The method of claim 12, wherein the electrical connection comprises a capacitive connection.

15. The method of claim 9, wherein the distance measuring device computes the distance in accordance with a first voltage difference between the inner voltage electrodes and a second voltage difference between the outer current electrodes.

16. The method according to claim 9, wherein the electrode further comprises a pair of reference electrodes, and wherein the distance measuring device computes the distance in accordance with a first voltage difference between the inner voltage electrodes and a second voltage difference between the reference electrodes.

17. The method according to claim 9, wherein the electrode further comprises a reference electrode, and wherein the distance measuring device computes the distance in accordance with a first voltage difference between one of the inner voltage electrodes and the reference electrode and a second voltage difference between the other inner voltage electrode and the reference electrode.

* * * * *